United States Patent
Wright

(10) Patent No.: US 8,361,093 B2
(45) Date of Patent: Jan. 29, 2013

(54) BAND FORMING APPARATUS

(75) Inventor: John T. M. Wright, Denver, CO (US)

(73) Assignee: Genesee BioMedical, Inc., Denver, CO (US)

( * ) Notice: Subject to any disclaimer, the term of this patent is extended or adjusted under 35 U.S.C. 154(b) by 249 days.

(21) Appl. No.: 12/693,193

(22) Filed: Jan. 25, 2010

(65) Prior Publication Data

US 2010/0191254 A1    Jul. 29, 2010

Related U.S. Application Data

(60) Provisional application No. 61/146,744, filed on Jan. 23, 2009.

(51) Int. Cl.
*A61B 17/08* (2006.01)
*A61B 17/00* (2006.01)

(52) U.S. Cl. .................................. 606/157; 606/203

(58) Field of Classification Search .......... 606/201–203, 606/151, 157, 74, 148, 232; 600/37; 24/17 A, 24/17 B, 17 AP, 712, 712.6
See application file for complete search history.

(56) References Cited

U.S. PATENT DOCUMENTS

| | | | |
|---|---|---|---|
| 4,042,979 A | 8/1977 | Angell | |
| 4,290,151 A | 9/1981 | Massana | |
| 5,064,431 A | 11/1991 | Gilbertson | |
| 5,306,296 A | 4/1994 | Wright | |
| 5,716,397 A | 2/1998 | Myers | |
| 5,824,066 A | 10/1998 | Gross | |
| 5,989,252 A | 11/1999 | Fumex | |
| 6,402,781 B1 | 6/2002 | Langberg | |
| 7,101,395 B2 | 9/2006 | Tremuliset | |
| 7,959,650 B2 * | 6/2011 | Kaiser et al. | 606/232 |
| 2007/0027533 A1 | 2/2007 | Douk | |

* cited by examiner

*Primary Examiner* — Julian Woo
(74) *Attorney, Agent, or Firm* — Swanson & Bratschun, L.L.C.

(57) ABSTRACT

A band forming apparatus for banding an internal body part and method of using same. The band forming apparatus is initially supplied as a relatively straight structure so that it can be, for example, inserted through a catheter or narrow incision such as when using endoscopic or robotic surgery techniques. Alternatively, the band forming apparatus may be used or inserted using conventional surgical techniques. In use, the initially straight assembly can be formed into a loop or band around an internal body part. Embodiments of the band forming apparatus include a compressible tube having first and second tube ends and an orifice in the tube wall between the first and second tube ends. A string is received in the tube, the string having a first end extending out of the first end of the tube and a second end extending out of the orifice. Alternatively the second string end may extend out of the second tube end. Means are provided for drawing an securing the band forming apparatus into a band of selected diameter.

12 Claims, 16 Drawing Sheets

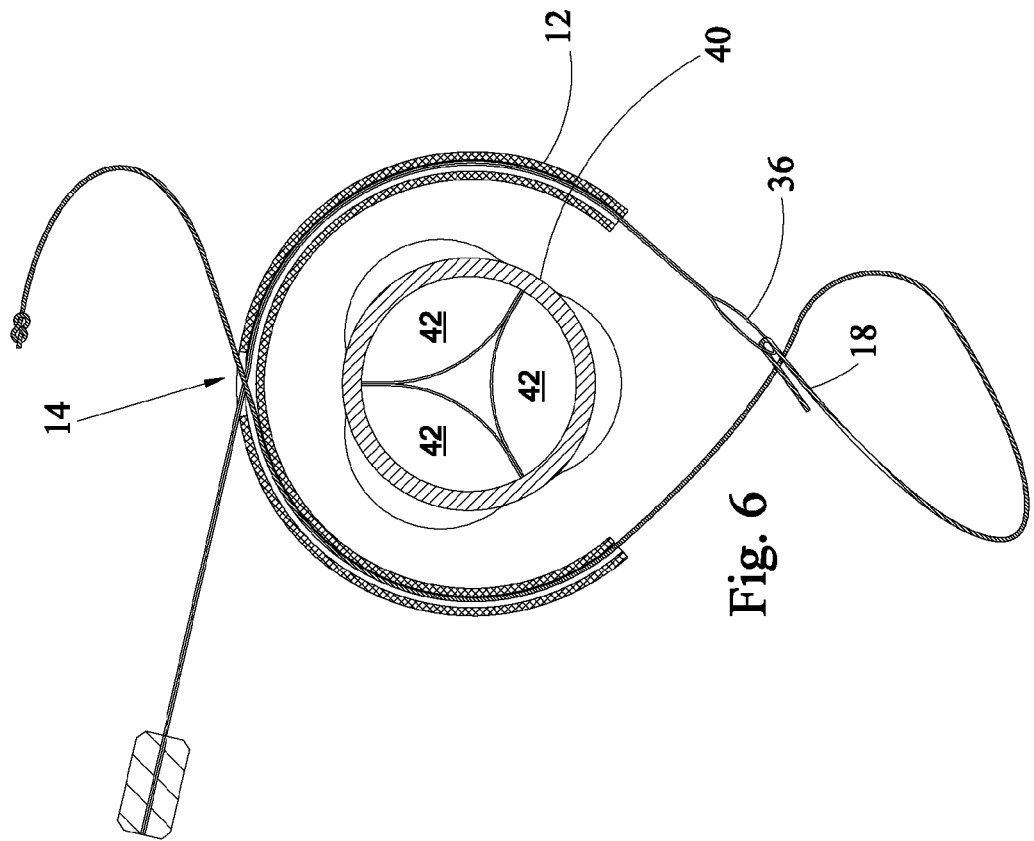
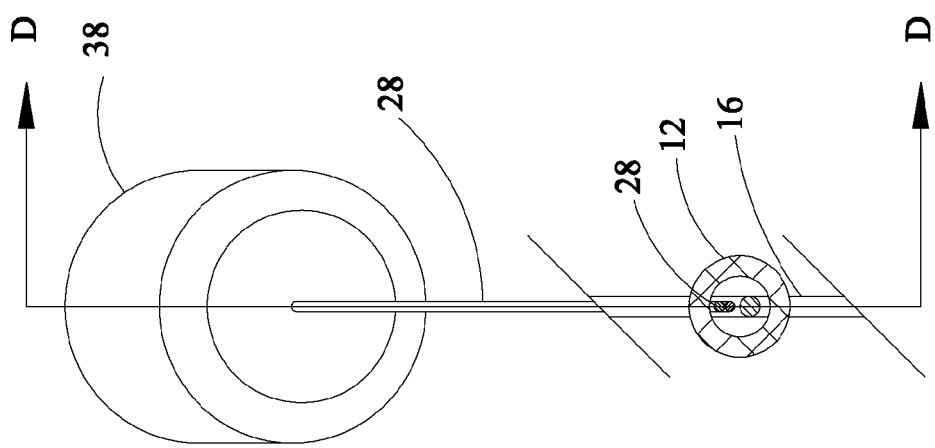

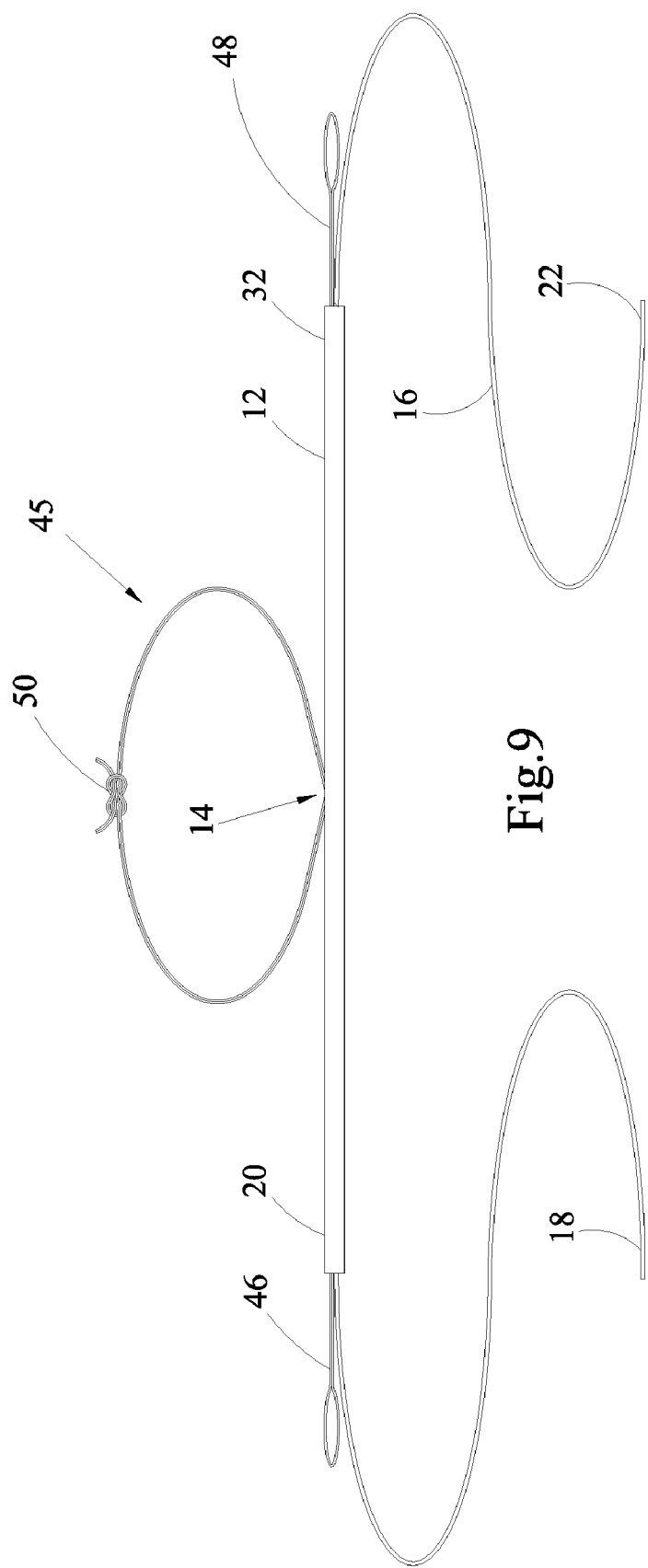

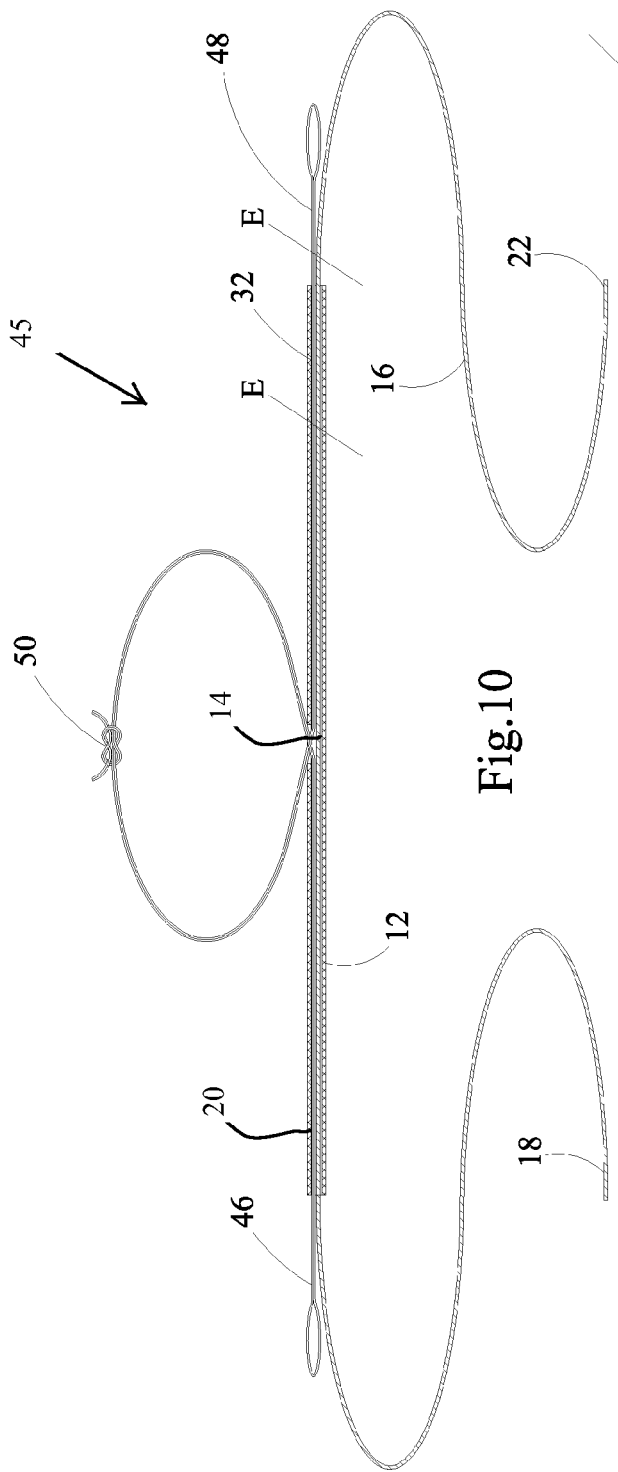
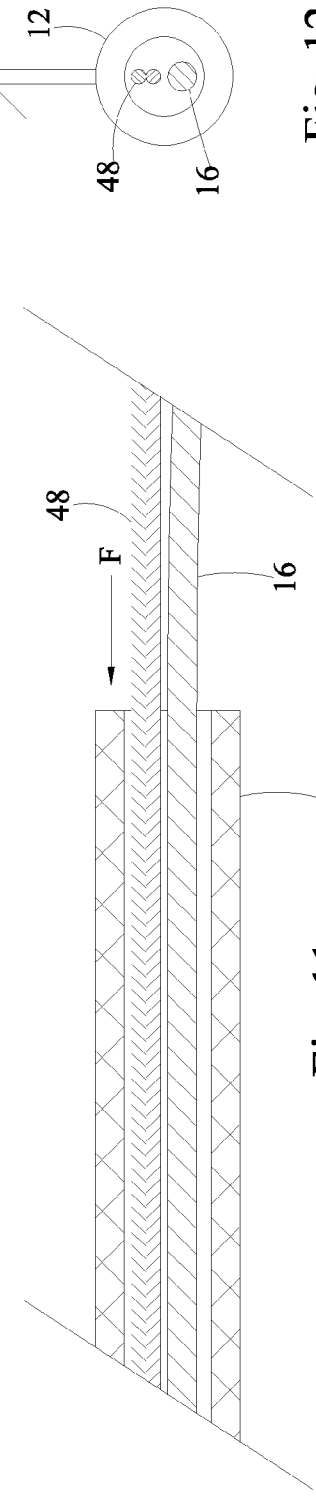

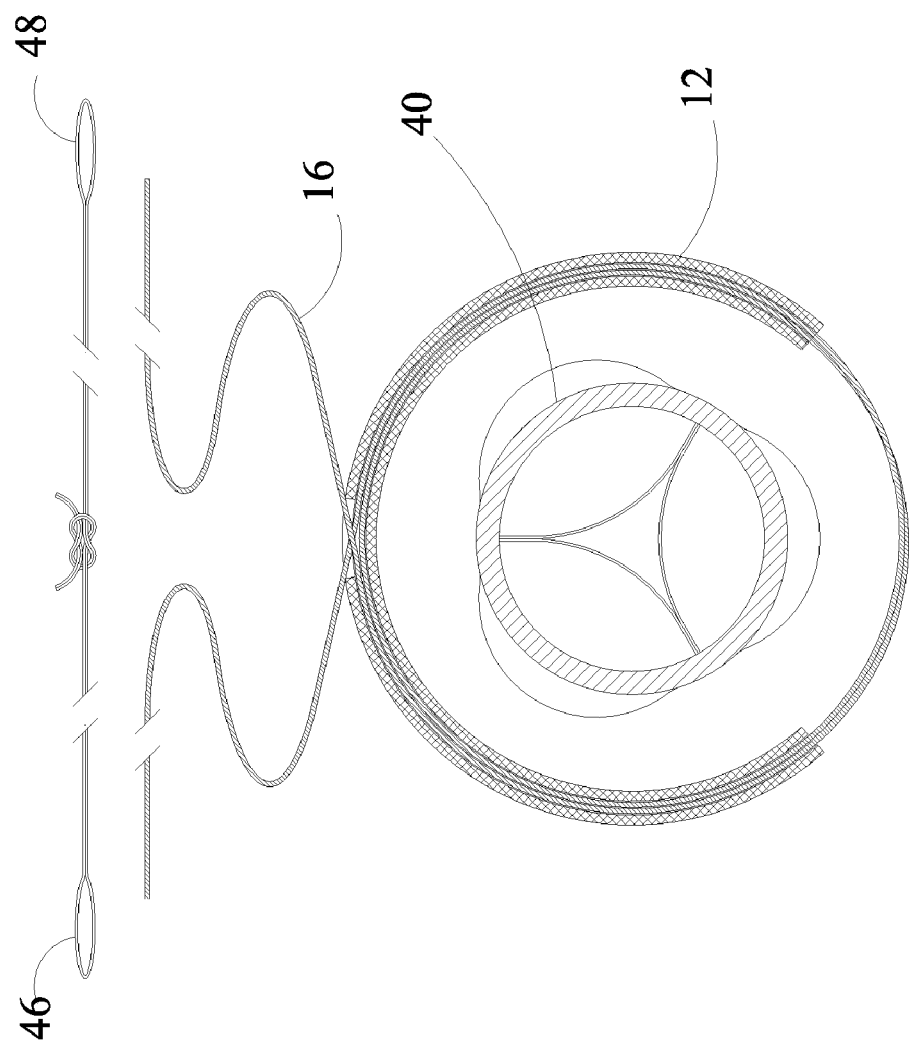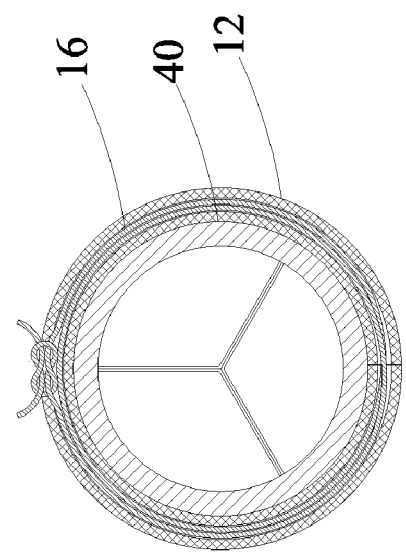
Fig. 16
Fig. 17

BAND FORMING APPARATUS

RELATED APPLICATIONS

This application claims priority from U.S. Provisional Patent Application Ser. No. 61/146,744, filed Jan. 23, 2009, entitled "Band Forming Apparatus," which is hereby incorporated by reference.

TECHNICAL FIELD

The disclosed embodiments are directed toward a surgical device, and more particularly toward an apparatus and method for forming a band about an internal body part.

BACKGROUND

There are various human disease and anatomical abnormalities that require vessel or body members to be controllably reduced in diameter. For example, an enlarged sino-tubular junction of the aorta may cause aortic valve insufficiency; similarly, a dilation of the ascending, transverse or descending aorta may lead to aortic aneurism. "Banding" of the pulmonary artery may be necessary in some pediatric congenital heart disease patients, and banding of the esophagus may be useful in the treatment of gastro-esophageal reflux disease. Moreover, banding the stomach may be used as one form of treating morbid obesity. Banding in this manner can be highly invasive, however, because the body part must be exposed for a physician to implant a band or ring around the effected body part.

The embodiments described herein are intended to overcome one or more of the problems discussed above.

SUMMARY OF THE EMBODIMENTS

One embodiment is a structure for forming a ring around a body part. The ring banding structure is initially supplied as a relatively straight structure so that it can be, for example, inserted through a catheter or narrow incision such as when using endoscopic or robotic surgery techniques. Alternatively, the ring banding structure may be used or inserted using conventional surgical techniques. Thereafter the straight assembly can be formed into a loop or band around an internal body part.

Embodiments of the band forming apparatus for banding an internal body part include a compressible tube having first and second tube ends and an orifice or hole in the tube wall between the first and second tube ends. A string is received in the tube, the string having a first string end extending out of the first end of the tube and a second string end extending out of the orifice. One embodiment of the apparatus further includes an instrument having an elongate body having a first end extending out of the second end of the tube and a second end extending out of the orifice. The first end of the elongate body includes means for securing the first end of the string.

A stop, which may comprise a knot, is provided in the second end of the string and is configured to prevent the second end of the string from being pulled into the orifice. The means of securing the first end of the string may include a loop. In such an embodiment the second end of the elongate body may comprise a stop configured to prevent the second end of the elongate body from being pulled into the orifice. In an alternative embodiment, the apparatus includes a plurality of compressible tubes attached together in a parallel array. Each of the tubes includes a string extending between the first end of the tube and an orifice between the tube ends. Such an embodiment further includes at least one of the tubes receiving the instrument in the manner described above.

In another alternative embodiment the band forming apparatus may include a string and two loop members configured to initially extend from the tube ends and ultimately be used to draw the string and tube into a looped band.

Another aspect of the invention is a method of forming a band around an internal body part. The method includes providing a band forming apparatus having a compressible tube having a first and second tube ends and an orifice in a tube wall between the first and second tube ends. A string is received in the tube, the string have a first string end extending out of the first end of the tube and a second string end extending out of the orifice. An instrument is provided having an elongate body with a first end extending out of the second end of the tube and the second end extending out of the orifice. The first end has means for securing the first end of the string. The method further includes inserting the band forming apparatus into a body in proximity to the internal body part. The tube is then bent around the internal body part and the first end of the string is inserted into the means for securing the first end of the string. The second end of the elongate body is then pulled to draw the first end of the elongate body into the second end of the tube with the first end of the string attached thereto, until the first end of the string extends out of the orifice. An overhand or other type of knot is then tied in the first and second string ends and the first and second string ends are pulled to form the tube into a band of a select diameter around the body part. Thereafter a second knot is tied between the first and second string ends to fix the select diameter of the band around the body part.

The method may further include providing a plurality of tubes attached in parallel to one another to form an array, each tube with a string received therein as described above. The method would then include repeating each of the steps described above to form a series of parallel bands around the body part.

The band forming apparatus and method described herein has application for the treatment of some or all of the pathological conditions described in the Background. The apparatus and method may also find application to treat enlarged aortic roots and provide adjustments to aortic root replacement grafts.

The band forming apparatus and method described herein may be used in the various applications described above by implanting the apparatus arthroscopically, endoscopically or using a surgical robot as well as using normal open chest surgical procedures. The device allows implantation and adjustment without cardiopulmonary bypass. Because the tube is made of a compressible material, the single size may be used in a wide range of patients for a wide variety of applications. The apparatus does not involve any sizing issues or require tools for sizing it and the apparatus may be simply adjusted to a desired diameter during implantation. Further, the band forming apparatus does not require a holder. In the particular case of a regurgitant aortic valve due to an enlarged sino-tubular junction, the apparatus may be adjusted while the level of the aortic regurgitation is monitored using transesophogeal echocardiography. The band may be controllably tightened until the aortic regurgitation disappears. The apparatus may be secured in position axially of the body part using a minimal number of sutures (e.g., three).

Application of the apparatus and method is not limited to aortic valve repair. It could be used wherever some sort of a band or ring structure around an internal body part is desired. The materials comprising the tube may be, but are not limited to, polymers and could include conductive materials such as a tube of braided stainless steel and the string could be a stainless steel wire.

BRIEF DESCRIPTION OF THE DRAWINGS

FIG. 4 is a cross-sectional view of the of the band forming apparatus of FIG. 1 taken in the direction of arrows CC of FIG. 1;

FIG. 6 is a cross-sectional view of the band forming apparatus of FIG. 1 in the direction of arrows DD of FIG. 4 with the first end of the string passed around a body part to be compressed.

FIG. 9 is a side elevation view of an alternative embodiment of a band forming apparatus;

FIG. 10 is a cross-sectional side elevation view of the band forming apparatus of FIG. 9;

FIG. 11 is a an enlarged cross-sectional side elevation view of the band forming apparatus of FIG. 9 between the lines EE of FIG. 10;

FIG. 12 is an end elevation view of the band forming apparatus of FIG. 9 taken in the direction of arrow F of FIG. 11;

FIG. 16 is a cross-sectional view of the band forming apparatus of FIG. 9 showing how the band forming apparatus of FIG. 9 is further formed into a loop around an internal body part;

FIG. 17 a cross-sectional view of the band forming apparatus of FIG. 9 showing how the band forming apparatus of FIG. 9 around an internal body part showing the string drawn tight and knotted;

DETAILED DESCRIPTION OF THE EMBODIMENTS

Figure 1:
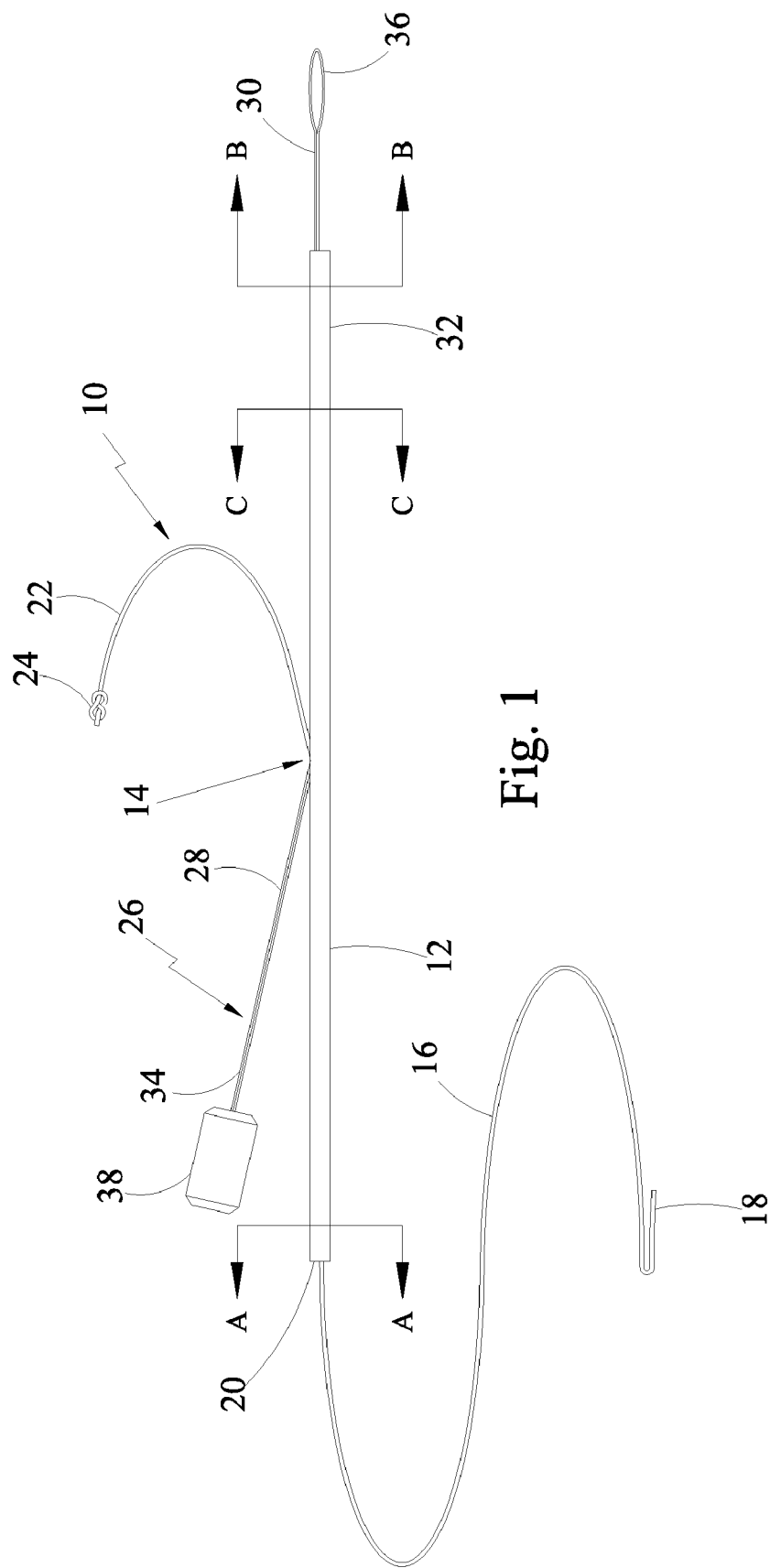
FIG. 1 is a side elevation of a first embodiment of a band forming apparatus.

FIG. 1 is a side elevation of a first embodiment of a band forming apparatus 10 in a partially assembled condition. The apparatus consists of an expanded Polytetrafluoroethylene (PTFE) tube 12 having opposing open ends. The tube could optionally be fabricated from other materials. In one embodiment an outside diameter of the tube may be 0.1 inches and the inside diameter may be 0.0625 inches. Other dimensions for various applications may be desirable. The tube could also be made of a material such as braided Polyester. The expanded PTFE tube however resists tissue ingrowth, unlike braided Polyester. In some instances, such as banding the pulmonary artery in children, tissue ingrowth is undesirable. An essential property of any tube material is that it be significantly axially compressible. Embodiments could include a tube made of conductive material such as braided stainless steel. Between the open ends of the tube an intermediate side hole or orifice 14 is provided in the tube wall.

A string 16 is received in the tube, the string having a first end 18 extending out of a first end 20 of the tube 12 and a second string end 22 extending out of the orifice 14. A stop such as knot 24 can be provided in the second end of the string to prevent it from being drawn into the orifice 14. The string may be formed of a monofilament polymer, such as 2/0 nylon suture or a braided string, for example a size 2 braided Polyester surgical suture may be used. Other materials may also be suitable for implementing the string 12. In an embodiment where the tube is made of braided stainless steel, a conductive material such as stainless steel wire may be advantageous for implementing the string element.

An instrument 26 including an elongate body 28 having a first end 30 extending out of the second end 32 of the tube and a second end 34 extending out of the orifice 14 is also shown on FIG. 1. A loop 36 may be provided at the second end of the elongate body 28 for securing the first end of the string 18 in a manner that will be described in greater detail below. A stop or retainer 38 (which may be made of plastic, metal or another suitable material) is provided at the second end of the elongate body 28 and is sized to prevent the second end of the elongate body 28 from being drawn into the orifice 14.

The elongate body 28 of the instrument 26 may be formed with a small diameter (e.g., 0.01 inch) of springy stainless steel wire or alternatively of a monofilament polymer, such as 2/0 nylon suture. If a monofilament polymer is used for the loop member a simple knot may serve to prevent the second end of the loop member from being inadvertently pulled into the orifice. A loop member made of a resilient (springy) material may be advantageous because the collapsible semi-rigid loop 36 formed at the first end and extending out of the second end of the tube may capture the first end of the string 18 to draw it through the tube and out the orifice in a manner described in greater detail below. A heat-set hairpin bend may be provided at the first end of the string 18 as depicted in FIG. 1. The heat-set hairpin bend makes it more convenient for the wire loop 36 to engage the string and also prevents the string from inadvertently being pulled into the first end 20 of the tube 12.

Figure 2:
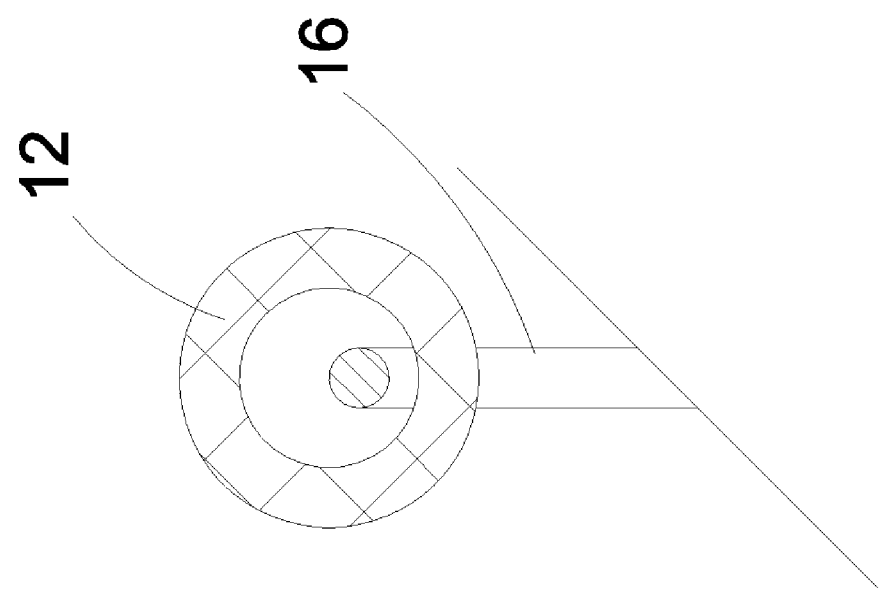
FIG. 2 is a cross-sectional view of the band forming apparatus of FIG. 1 in the direction of arrows AA of FIG. 1.

FIG. 2 shows a cross-sectional view of the band forming apparatus 10 in the direction of arrows AA of FIG. 1.

Figure 3:
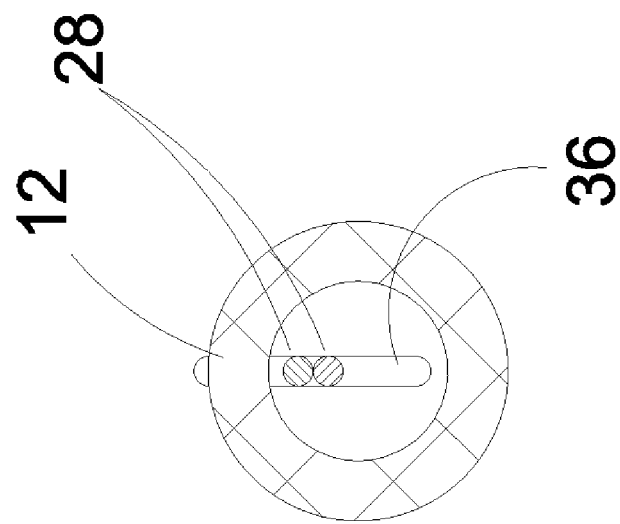
FIG. 3 is a cross-sectional view of the band forming apparatus of FIG. 1 in the direction of arrows BB of FIG. 1.

FIG. 3 shows a cross-sectional view of the band forming apparatus 10 in the direction of arrows BB of FIG. 1

FIG. 4 shows a cross-sectional view of the of the band forming apparatus 10 shown in FIG. 1 taken in the direction of arrows CC of FIG. 1.

Figure 5:
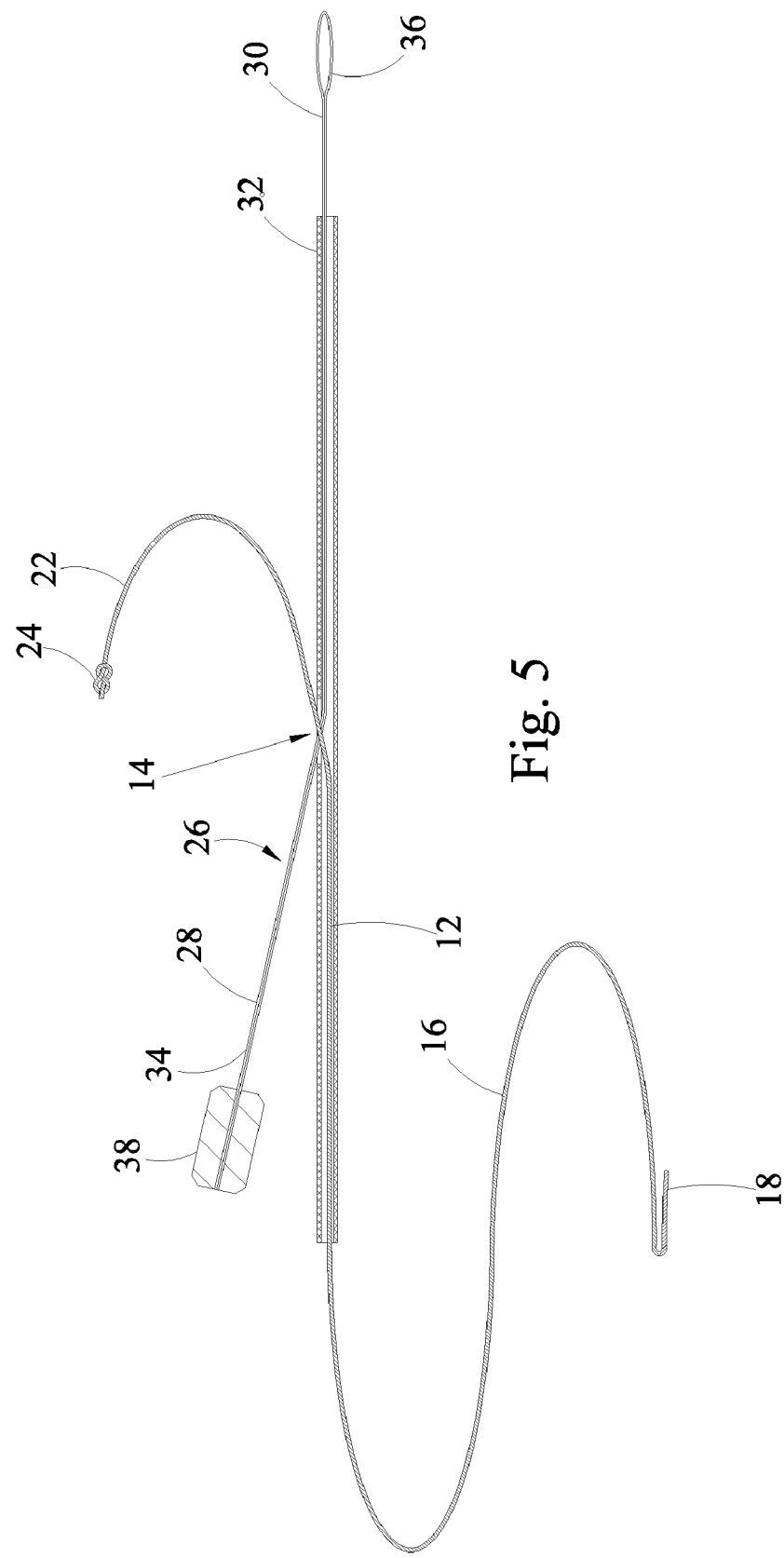
FIG. 5 is a cross-sectional view of the band forming apparatus of FIG. 1 in the direction of arrows DD of FIG. 4.

FIG. 5 shows a cross-sectional view of the band forming apparatus 10 in the direction of arrows DD of FIG. 4.

FIG. 6 shows a cross-sectional view in the direction of arrows DD of FIG. 4 of the band forming apparatus 10 with the first end of the string 18 passed around a body part to be compressed 40. The representative body part 40 shown diagrammatically in the figures is an enlarged sino-tubular region of the aorta and thus consequentially includes incompetent aortic valve leaflets 42. As noted above, the various embodiments of the band forming apparatus 10 can be used upon many different types of body part. In the FIG. 6 position, the first end 18 of the string 12 is passed through the loop 36 extending from the second end of the tube 32. The second end of the instrument 26 is shown extending from the intermediate orifice 14. In use, the instrument may be retracted, causing the first end of the string 18 to be pulled through the intermediate orifice 14 and the loop instrument 26 removed from the tube.

Figure 7:
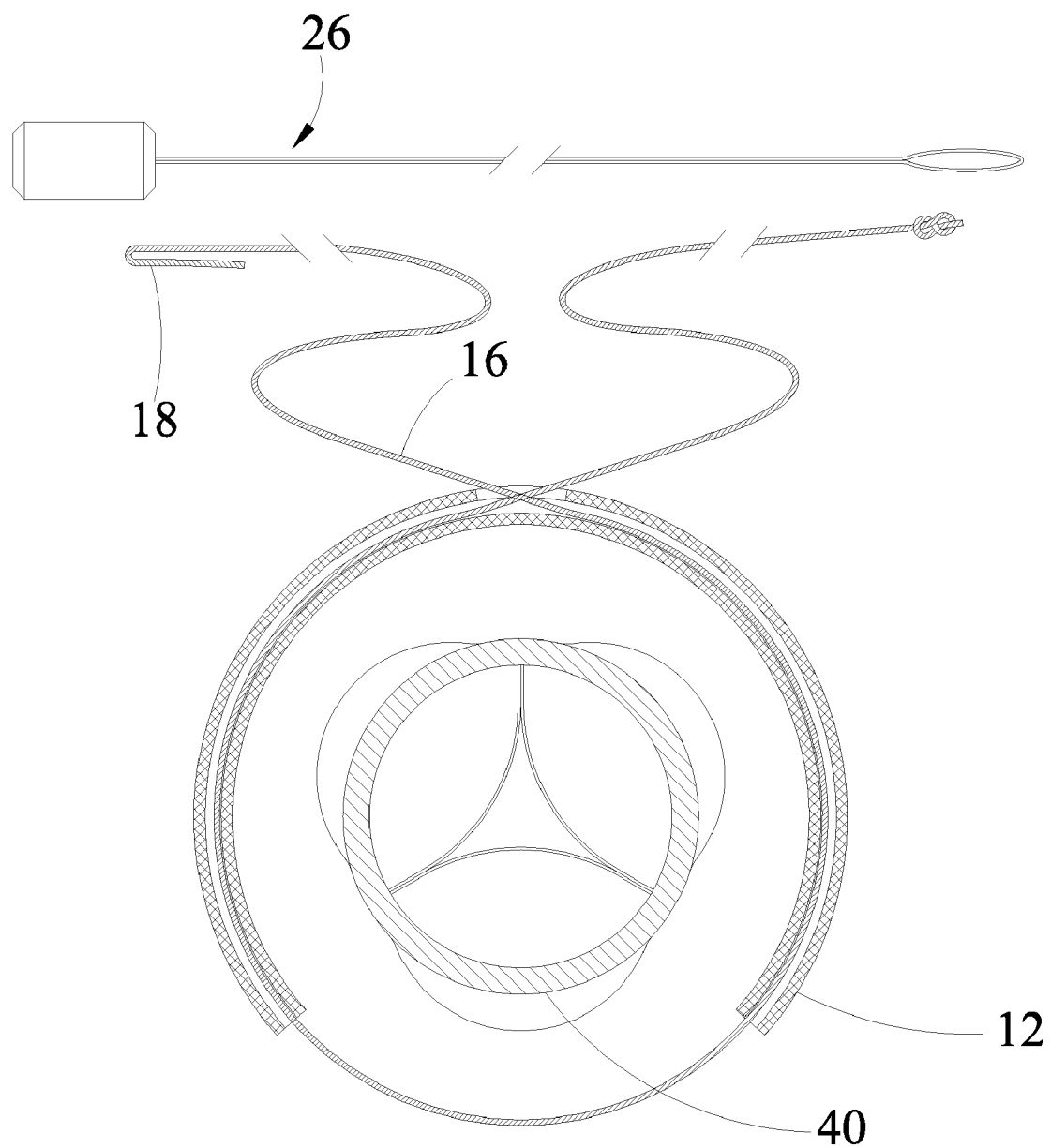
FIG. 7 is a cross-sectional view of the band forming apparatus of FIG. 1 in the direction of arrows DD of FIG. 4.

FIG. 7 shows a cross-sectional view of the band forming apparatus 10 in the direction of arrows DD of FIG. 4 with the first end of the string 18 pulled though the central orifice, and the instrument 26 removed from the tube 12.

Figure 8:
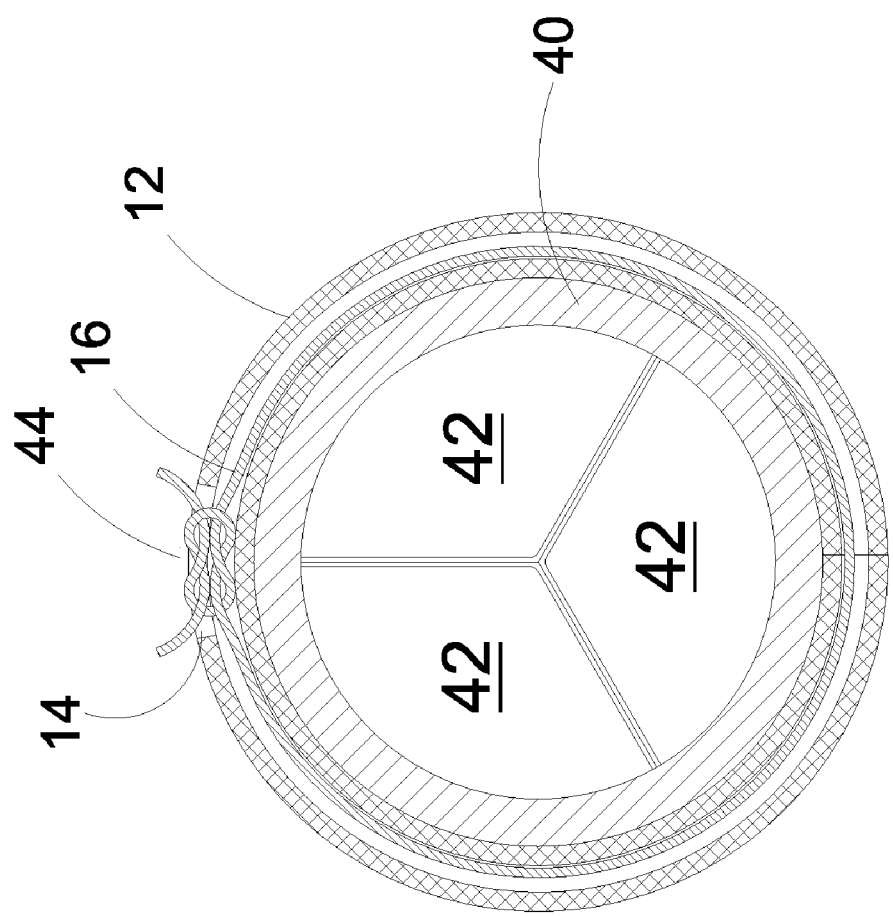
FIG. 8 is a cross-sectional view of the band forming apparatus of FIG. 1 in the direction of arrows DD of FIG. 4 after the strings have been tightened.

FIG. 8 shows a cross-sectional view of the band forming apparatus 10 in the direction of arrows DD of FIG. 4 after the two ends of the string 12 have been pulled sufficiently tightly and tied in a knot. Typically the first and second ends are tied in an overhand knot and pulled to tighten the band as discussed below, and then a second overhead knot is tied to form the square knot 44 depicted in FIG. 8. As shown on FIG. 8, the two ends of the tube have been brought together and the tube has been contracted by the tightening and knotting of the string 12. Thus, the sino-tubular junction of the aorta (body part 40) has been compressed by the band forming apparatus 10. The aortic valve leaflets 42 now coapt correctly and the prior aortic insufficiency corrected. By forming the knot at the orifice 14 instead of at the tube ends, crumpling of the tube forming the final band is prevented.

FIG. 9 shows an alternate embodiment of a band forming apparatus 45 in a partially assembled condition, with like reference numbers identifying like parts with respect to FIGS. 1-8.

FIG. 10 is a cross-sectional side elevation view of the alternative embodiment of the band forming apparatus 45 of FIG. 9. The tube 12 may consist of an expanded Polytetrafluoroethylene (PTFE) tube having opposing open ends 20, 32. The tube 12 could also be made of a material such as braided polyester. An essential property of any material is that it be significantly axially compressible. Between the open ends 20, 32 an intermediate orifice 14 is provided in the tube sidewall. The tube contains a string 16 and partially contains two loop members 46, 48. One end of the loop member 46 is shown extending from the first end 20 of the tube and the other end of loop member is shown extending from the intermediate orifice 14. One end of the second loop end member 48 is shown extending from the second end 32 of the tube with the other end of the second loop end member 48 extending from the intermediate orifice 14. A knot 50 may be used to join the two ends of the loop members extending from the orifice 14 to prevent the distal ends of the loop members from being inadvertently pulled into the tube 12. As depicted in FIG. 9, the first end 18 of the string 16 (for example, a size 2 braided Polyester surgical suture) is shown extending from the first end 20 of the tube 12 and the second end 22 of the string 16 is shown extending from the second end 32 of the tube 16.

FIG. 11 shows an enlarged cross-sectional side elevation view of the band forming apparatus 45 between the lines EE of FIG. 10.

FIG. 12 shows an end elevation view of the band forming apparatus 45 taken in the direction of arrow F of FIG. 11.

Figure 13:
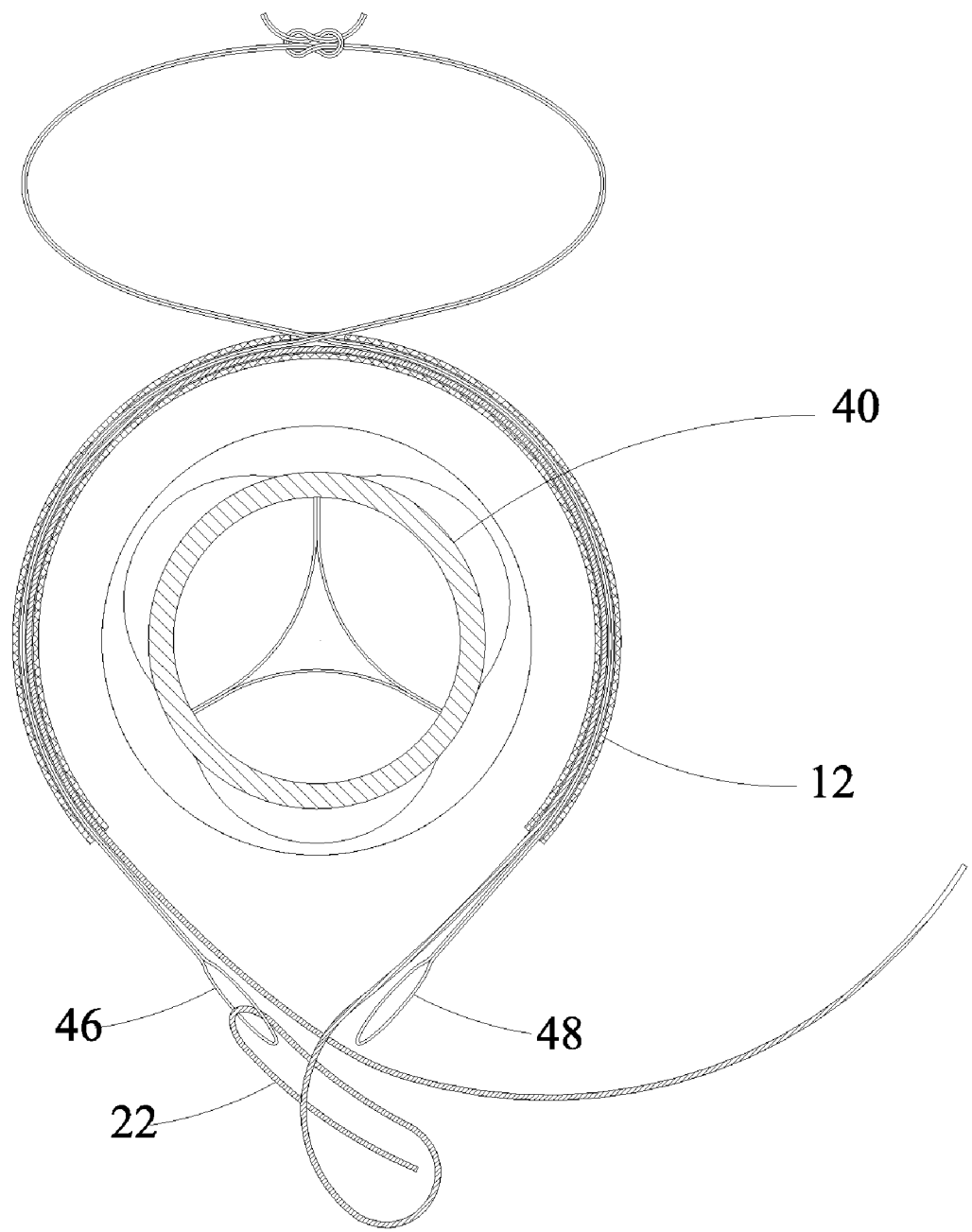
FIG. 13 is a cross-sectional view of the band forming apparatus of FIG. 9 showing how the band forming apparatus of FIG. 9 is initially formed into a loop around an internal body part.
Figure 14:
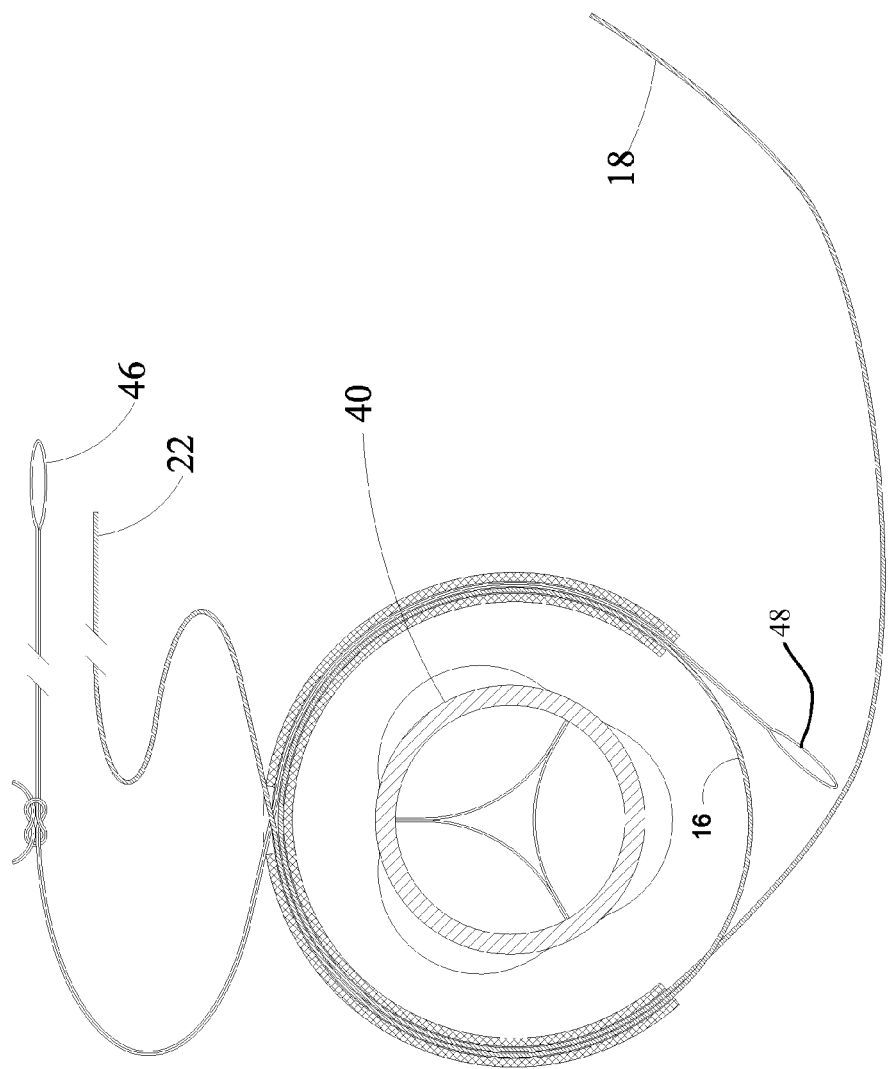
FIG. 14 is a cross-sectional view of the band forming apparatus of FIG. 9 showing how the band forming apparatus of FIG. 9 is further formed into a loop around an internal body part.

FIG. 13 is a cross-sectional view showing how the band forming apparatus 45 of FIG. 9 is formed into a loop around an internal body part. In this case the representative body part 40 is a sino-tubular junction of an aorta. Referring to FIG. 13, the tube 12 is formed in an arc around the body part 40 and the second free end 22 of the string 16 is fed through the opposite loop 46 of the first proximal loop member. The loop 46 is drawn through the tube, bringing the string with it and both may be removed through the intermediate orifice 14 in the tube. The result is illustrated in FIG. 14.

Figure 15:
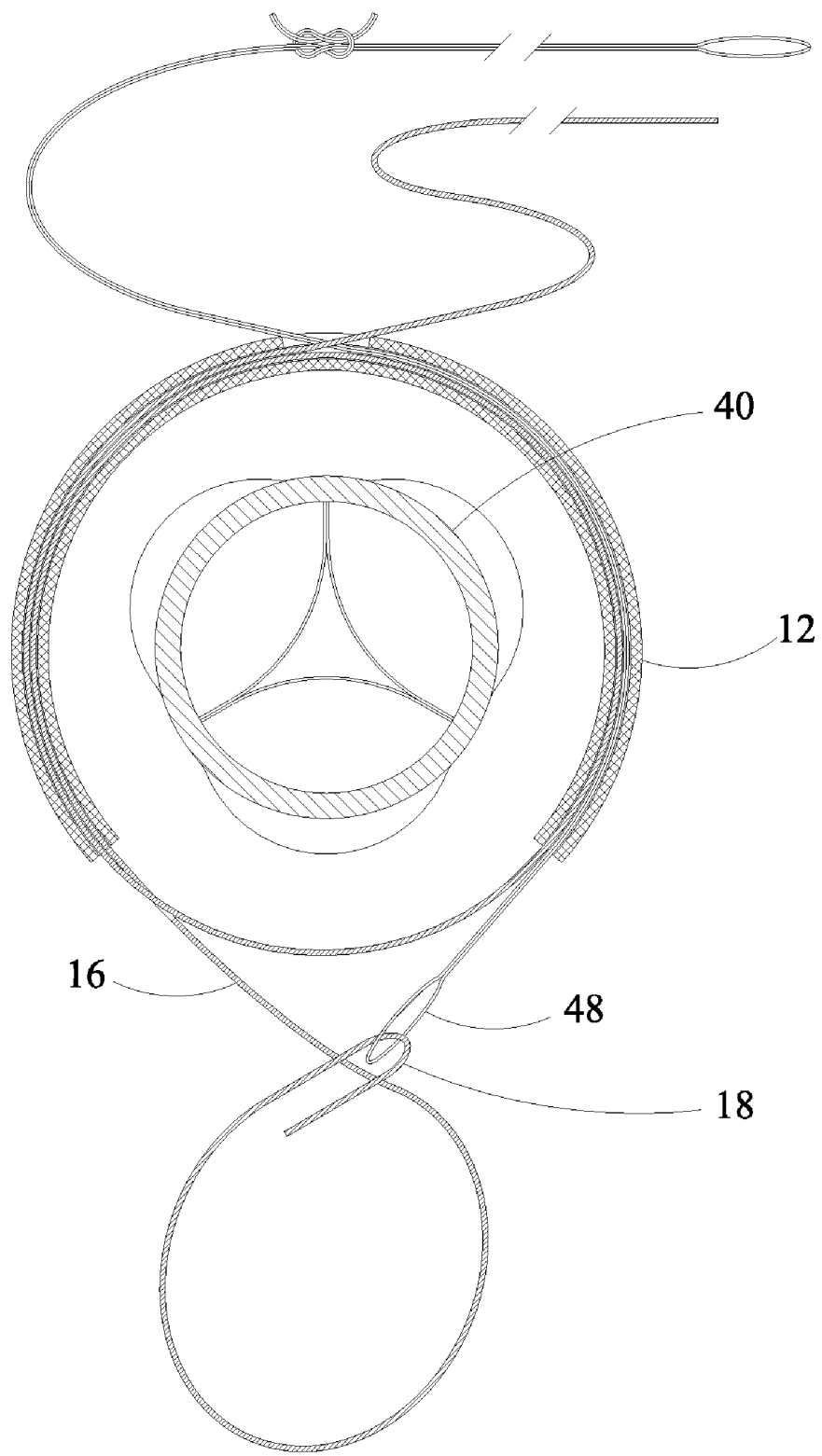
FIG. 15. a cross-sectional view of the band forming apparatus of FIG. 9 showing how the band forming apparatus of FIG. 9 is further formed into a loop around an internal body part.

Referring to FIG. 15, the process is then repeated with the opposite end 18 of the string 16 and second loop member 48 resulting in a loop around the body part 40 as illustrated in FIG. 16.

Referring to FIG. 16, the ends of the string 16 are pulled to form the tube into a ring and thereafter, as depicted in FIG. 17 the ring can be drawn to a desired size (compressing the tube material and body part as necessary) and then permanently fixed into a ring configuration by tying the ends of the string 16 together and clipping off the excess as depicted in FIG. 17.

Figure 18:
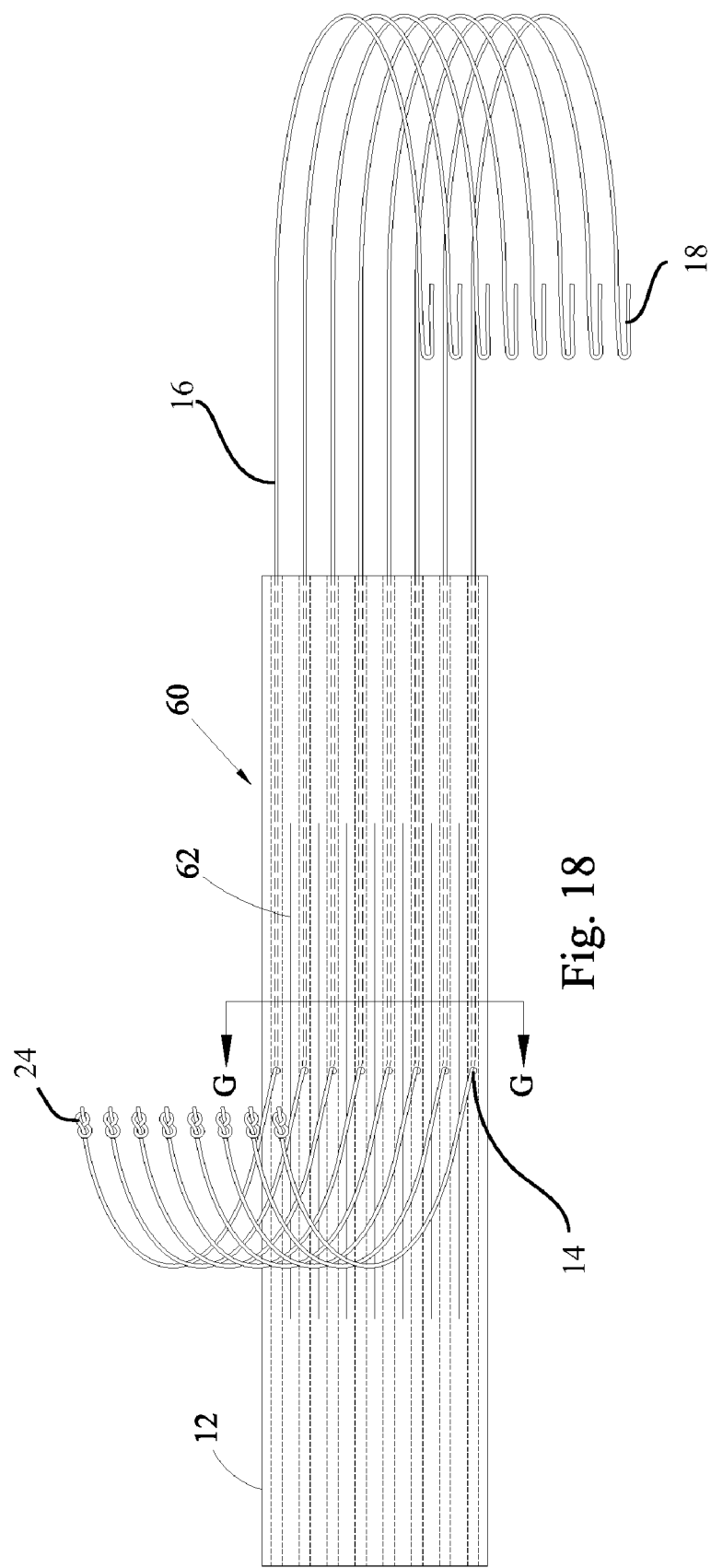
FIG. 18 is a front perspective view of an alternative band forming apparatus including an array of tubular members.
Figure 20:
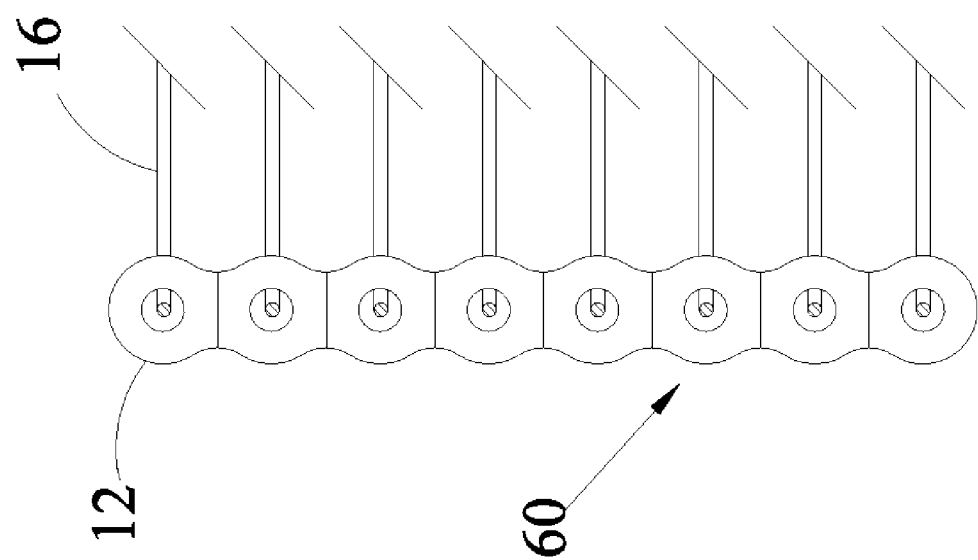
FIG. 20 is an enlarged cross-sectional view of the band forming apparatus of FIG. 18 taken along arrows GG of FIG. 18.
Figure 19:
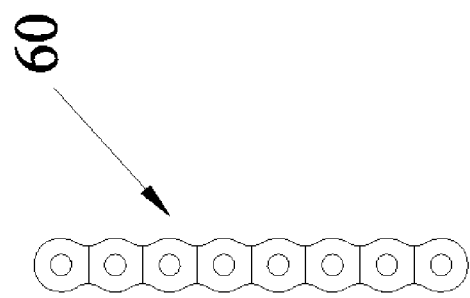
FIG. 19 is an end elevation view of the band forming apparatus of FIG. 18.

The width of the band forming apparatus and accordingly the width of the zone of constriction on a body part is related in the above described embodiments to the width of the tube 12. A wider zone of constriction may be achieved by utilizing multiple tubes which can if desired be arranged in an array of tubes. For example, referring to FIG. 18 an array 60 of compressible tubular members 12 (eight members are shown in FIG. 18 but more or less may be used) is shown, containing eight channels shown in the end elevation of FIG. 19. The mid-sections of the tubes 12 in the array 60 may contain seven slits 62 that pass between the walls as shown in FIG. 20 which is an enlarged cross-section taken along arrows GG of FIG. 18.

As shown in FIG. 18 eight strings 16 are passed into eight intermediate orifices or holes 14, and emerge at the first end of the array. The proximal ends of the strings may be terminated by heat-set hairpin bends 18 and the distal ends may be terminated in knots 24, as shown in FIG. 18.

Figure 21:
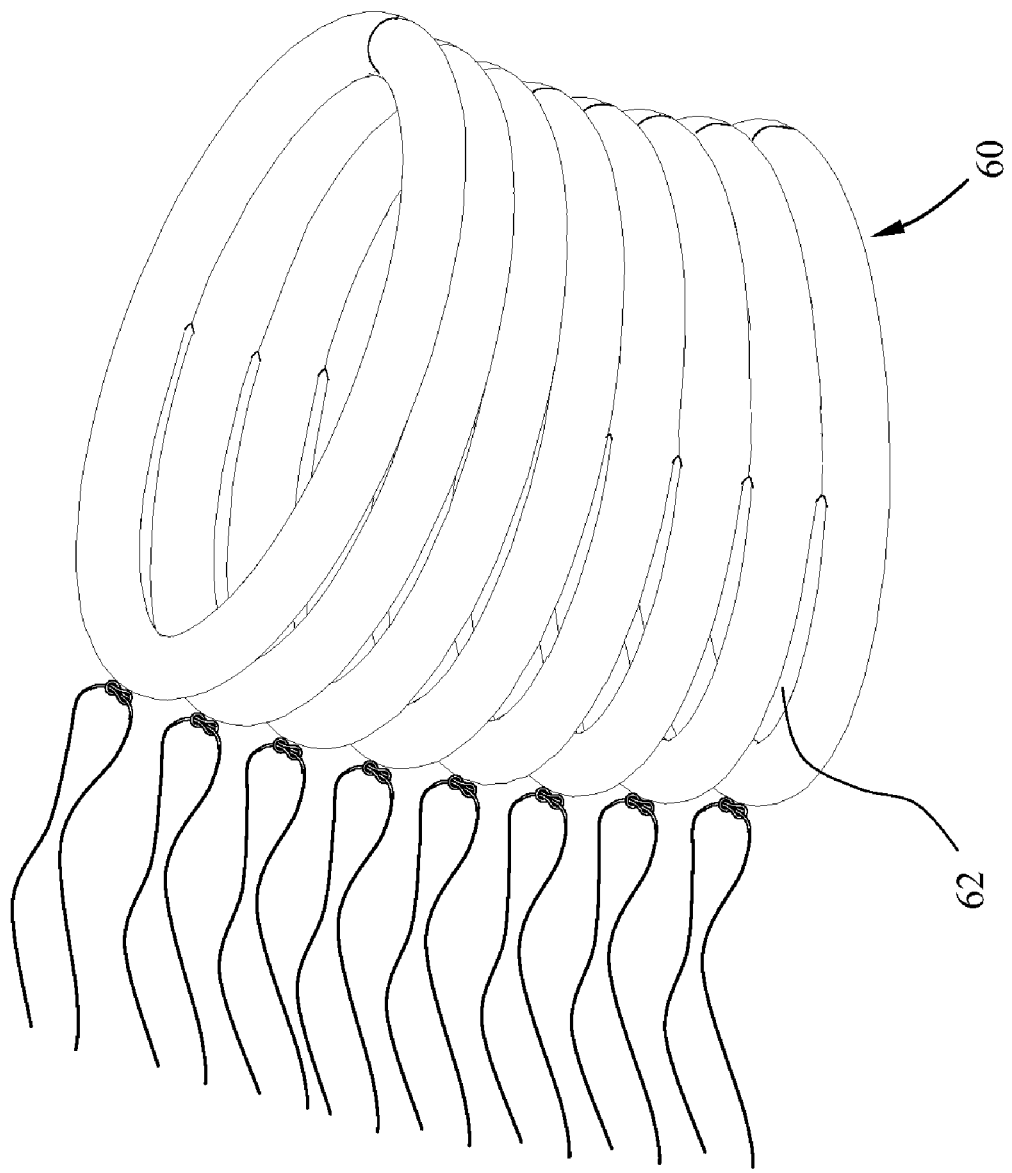
FIG. 21 is a perspective view of the band forming apparatus of FIG. 18 after the apparatus has been formed into a loop.
Figure 22:
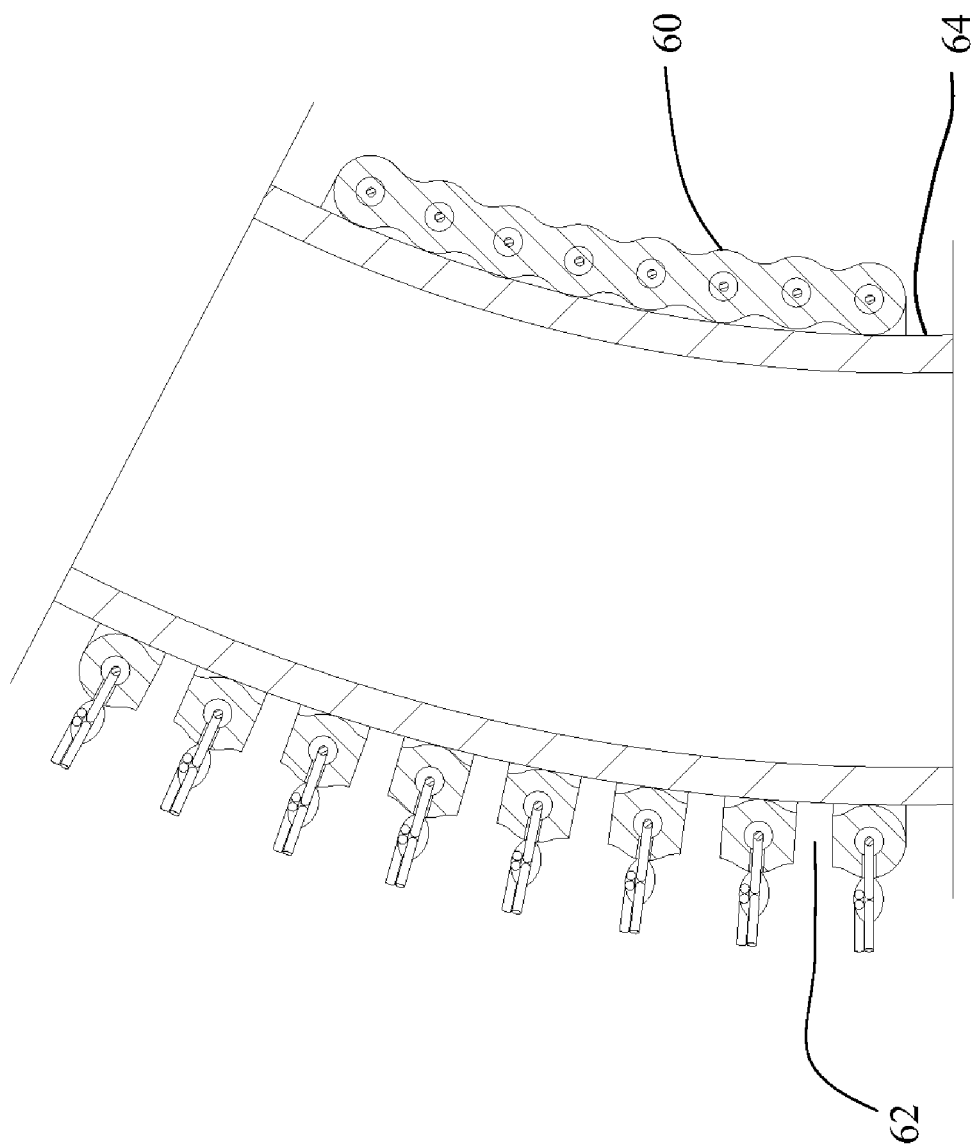
FIG. 22 is a cross-sectional view of the band forming apparatus of FIG. 18 configured in a loop as shown in FIG. 21.

One particular application of the array 60 is the reinforcement and subsequent contraction of an expanded ascending aorta by forming eight string loops around the aorta. For simplicity, an isolated loop member or instrument 26, such as is depicted in FIG. 1, may be passed in turn through each of the intermediate holes 14 in the array, threading the respective end of the string into the loop and withdrawing the loop and hence the end of the string from the intermediate hole. This is repeated for the remaining seven intermediate holes 14. The ends of the string pairs are tightened and tied as shown in FIG. 21. The partial slits 62 allow the outside of the curved ascending aorta 64 to be followed by the array, as shown in cross-section in FIG. 22.

When an apparatus as described herein is used for the "banding" of the pulmonary artery in pediatric congenital heart disease patients, subsequent adjustment of the banding may be required as the patient grows. It is therefore preferable that the string ends from the band be passed though a suitable length and diameter of flexible plastic tubing that is terminated just below the skin so that the adjustment knot (or other suitable adjustment means) may be readily available through a small skin incision, and the appropriate shortening of lengthening of the string may be undertaken without major invasive surgery.

Various embodiments of the disclosure could also include permutations of the various elements recited in the claims as if each dependent claim was a multiple dependent claim incorporating the limitations of each of the preceding dependent claims as well as the independent claims. Such permutations are expressly within the scope of this disclosure.

While the various embodiments have been particularly shown and described with reference to a number of embodiments, it would be understood by those skilled in the art that changes in the form and details may be made to the various embodiments disclosed herein without departing from the spirit and scope of the invention and that the various embodiments disclosed herein are not intended to act as limitations on the scope of the claims. All references cited herein are incorporated in their entirety by reference.

What is claimed is:

1. A band forming apparatus for banding an internal body part, the band forming apparatus comprising:
    a compressible tube having first and second tube ends and an orifice in a wall defining the tube between the first and second tube ends;
    a string received in the tube, the string having a first string end extending out of the first end of the tube and a second string end extending out the orifice; and
    an instrument comprising an elongate body having a first end extending out of the second end of the tube and a second end extending out of the orifice, the first end of the instrument having means for securing the first end of the string with the first end of the string extending out of the first end of the tube.

2. The band forming apparatus of claim 1 further comprising a stop at the second end of the string configured to prevent the second end of the string from being pulled into the orifice.

3. The band forming apparatus of claim 2 wherein the stop comprises a knot in the second end of the string.

4. The band forming apparatus of claim 1 wherein the means for securing the first end of the string comprises a loop.

5. The band forming apparatus of claim 1 wherein elongate body comprises a flexible shaft.

6. The band forming apparatus of claim 1 wherein the second end of the elongate body comprises a stop configured to prevent the second end of the elongate body from being pulled into the orifice.

7. The band forming apparatus of claim 1 further comprising a hook formed in the first end of the string.

8. The band forming apparatus of claim 1 further comprising the first end of the string received in the means for securing the first end of the string.

9. The band forming apparatus of claim 8 further comprising the first end of the string being inserted into the second end of the tube with the first end of the elongate body pulled away from the orifice.

10. The band forming apparatus of claim 1 further comprising a plurality of compressible tubes attached together in a parallel array, each with a string extending between the first end of the tube and an orifice between tube ends and one of the tubes receiving the instrument as recited in claim 1.

11. A band forming apparatus for banding an internal body part, the band forming apparatus comprising:
    a compressible tube having first and second tube ends and an orifice in a wall defining the tube between the first and second tube ends;
    a string received in the tube, the string having a first string end extending out of the first end of the tube and a second string end extending out the second end of the tube;
    a first loop member having a loop end extending from the first end of the tube and a second end extending from the orifice; and
    a second loop member having a loop end extending from the second end of the tube and a second end extending from the orifice.

12. The band forming apparatus of claim 11 further comprising a plurality of compressible tubes attached together in a parallel array.

* * * * *